United States Patent
Villefrance

(10) Patent No.: US 6,695,826 B2
(45) Date of Patent: Feb. 24, 2004

(54) VENTING/FILTER ASSEMBLY, BAG INCORPORATING SAME AND METHOD OF VENTING FLATUS GASSES

(75) Inventor: Tine Villefrance, Herlev (DK)

(73) Assignee: Dansac A/S, Fredensborg (DK)

(*) Notice: Subject to any disclaimer, the term of this patent is extended or adjusted under 35 U.S.C. 154(b) by 0 days.

(21) Appl. No.: 10/319,770

(22) Filed: Dec. 13, 2002

(65) Prior Publication Data

US 2003/0100870 A1 May 29, 2003

Related U.S. Application Data

(63) Continuation of application No. 09/568,318, filed on May 9, 2000, now Pat. No. 6,506,184.

(51) Int. Cl.[7] .................................................. A61F 13/15
(52) U.S. Cl. ...................................................... 604/333
(58) Field of Search ................................... 604/332–345

(56) References Cited

U.S. PATENT DOCUMENTS

| | | |
|---|---|---|
| 4,274,848 A | 6/1981 | La Gro |
| 4,419,100 A | 12/1983 | Alexander |
| 4,668,258 A | 5/1987 | Steer |
| 4,778,601 A | 10/1988 | Lopatin et al. |
| 4,983,171 A | 1/1991 | Schirmer |
| 5,074,851 A | 12/1991 | Plass et al. |
| 5,085,652 A | 2/1992 | Johnsen et al. |
| 5,167,650 A | 12/1992 | Johnsen et al. |
| 5,250,042 A | 10/1993 | Torgalkar et al. |
| 5,306,264 A | 4/1994 | Ferguson et al. |
| 5,370,638 A | 12/1994 | Keyes |
| 5,401,264 A | 3/1995 | Leise, Jr. |
| 5,417,678 A | 5/1995 | Baumann et al. |
| 5,468,235 A | 11/1995 | La Gro |
| 5,643,234 A | 7/1997 | Lesko |
| 5,672,163 A | 9/1997 | Ferreira et al. |
| 5,690,623 A | 11/1997 | Lenz et al. |
| 6,432,093 B1 * | 8/2002 | Shiina ......................... 604/333 |
| 6,506,184 B1 * | 1/2003 | Villefrance ................. 604/333 |

FOREIGN PATENT DOCUMENTS

| | | | |
|---|---|---|---|
| EP | 0283612 A1 | 9/1988 | |
| EP | 0336539 A1 | 10/1989 | |
| EP | 0443728 B1 | 8/1991 | |
| EP | 0516094 A1 | 12/1992 | |
| EP | 1 051 955 A2 * | 11/2000 | ........... A61F/5/441 |
| GB | 2 059 797 B | 4/1984 | |
| GB | 2 139 501 B | 1/1987 | |
| GB | 2 149 306 B | 2/1987 | |
| GB | 2 260 660 A | 7/1996 | |

* cited by examiner

Primary Examiner—Weilun Lo
Assistant Examiner—M. Bogart
(74) Attorney, Agent, or Firm—Marshall, Gerstein & Borun LLP

(57) ABSTRACT

A bag for receiving waste discharge from a human body, and the venting/filter assembly for such a bag, are disclosed. The combination includes a filter for deodorizing gas vented through an aperture in one wall of the bag and a gas-permeable barrier membrane disposed between the filter and the interior of the bag so that all gas exiting the bag flows through the membrane. The barrier membrane comprises an unlaminated microporous film of ultra high molecular weight polyethylene impermeable to waste liquids and solids and having a porosity capable of blocking the passage of bacteria and, preferably, at least some viruses. A method of so venting flatus gasses while preventing the escape of microorganisms is also disclosed.

4 Claims, 4 Drawing Sheets

Figure 2:
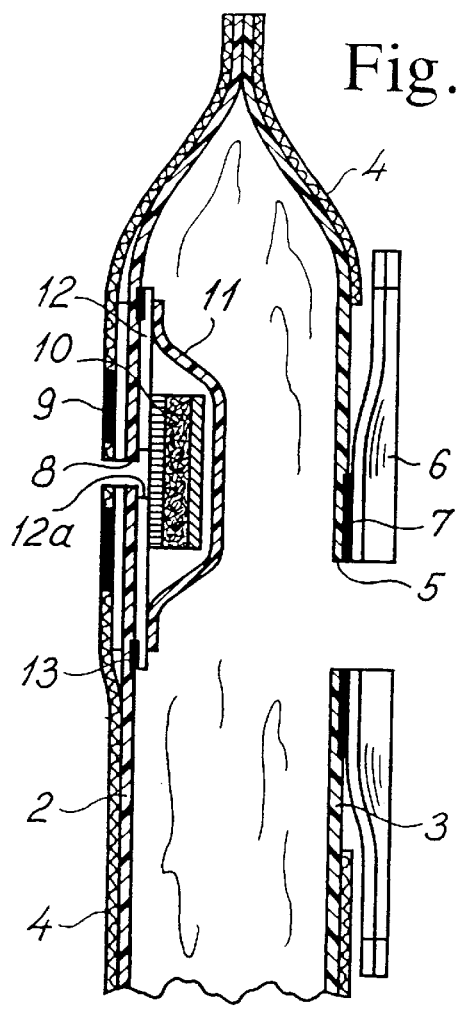

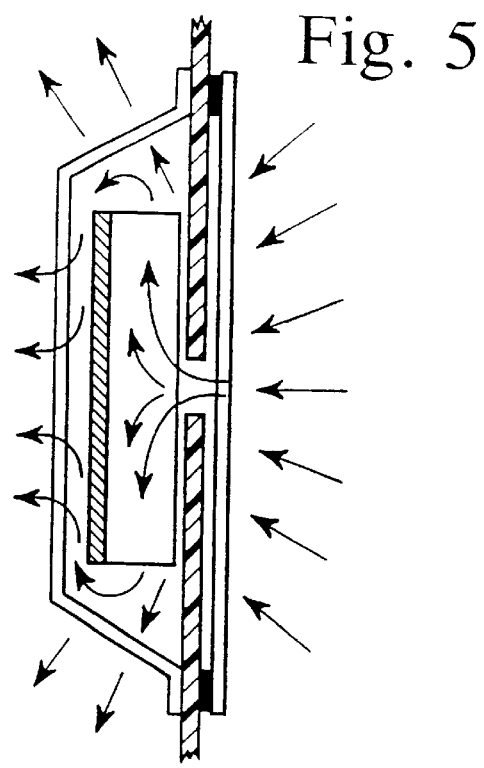
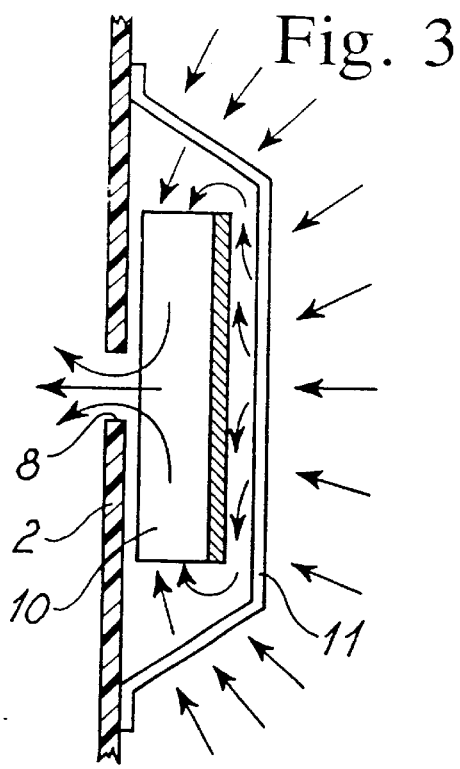
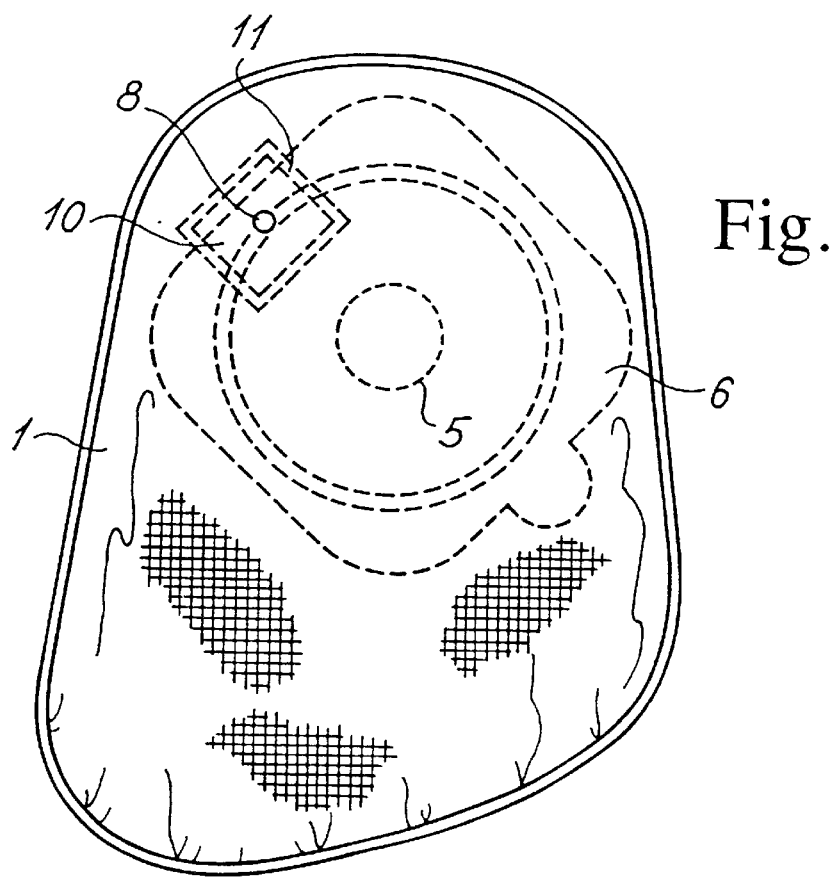

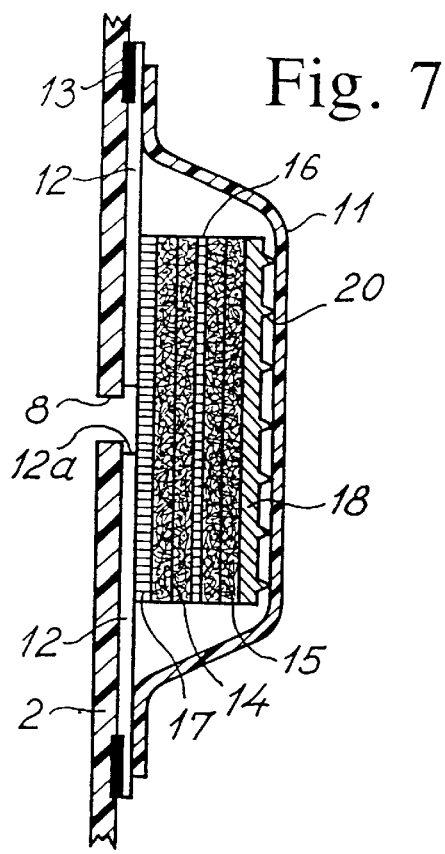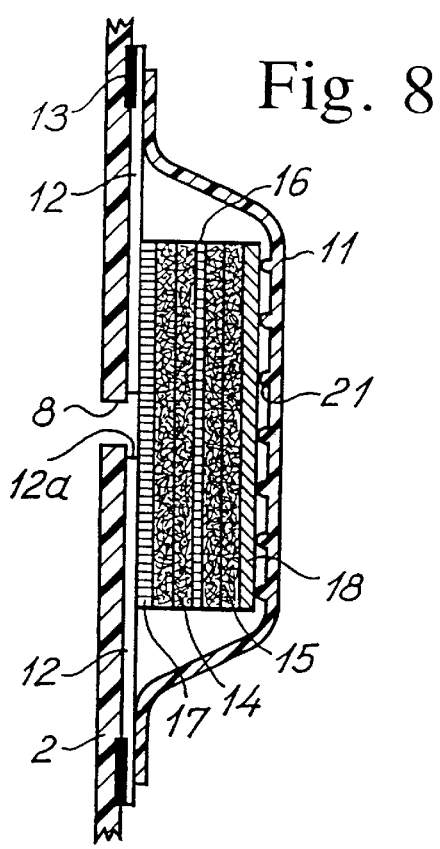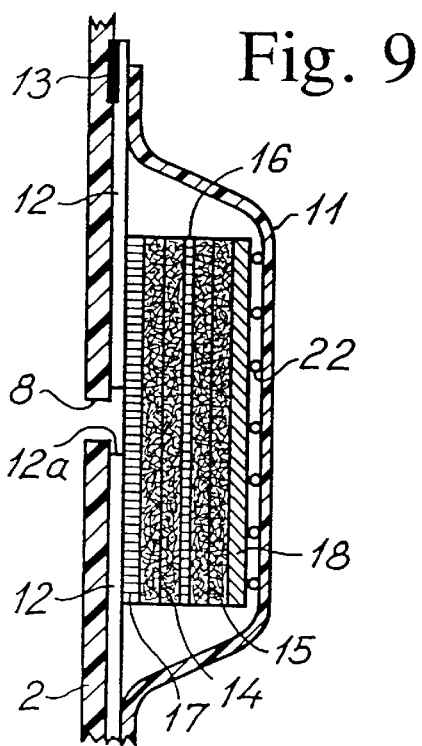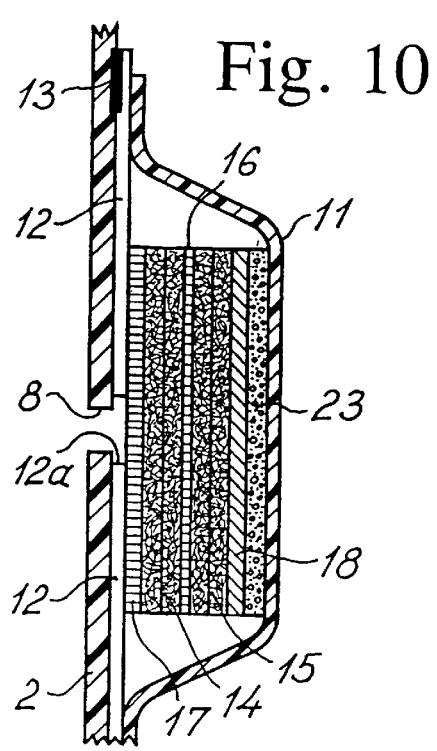

VENTING/FILTER ASSEMBLY, BAG INCORPORATING SAME AND METHOD OF VENTING FLATUS GASSES

REFERENCE TO RELATED APPLICATIONS

This application is a Continuation of U.S. patent application Ser. No. 09/568,318, filed May 9, 2000, now U.S. Pat. No. 6,506,184 B1, issued Jan. 14, 2003.

BACKGROUND AND SUMMARY

The present invention relates to a bag or pouch for receiving discharge from the human body, said bag comprising a distal wall and a proximal wall, each of a gas and liquid impermeable, heat sealable thermoplastic material and having the edges thereof sealed together and defining the interior of the bag between the walls, the proximal wall having a stomal aperture, and one of the walls having a gas venting aperture spaced from the stomal aperture, a filter for de-odorizing gas vented through the gas venting aperture and arranged such that all the gas exiting the bag through the venting aperture flows through the filter and an intermediate barrier membrane arranged intermediate the filter and the interior of the bag such that all the gas exiting the bag through the filter flows through the barrier membrane and for preventing liquids and solids in the interior of the bag from contacting the filter while allowing gas to flow through the barrier membrane from the interior of the bag to the filter.

Bags or pouches for the use of colostomy and ileostomy patients require a very efficient and reliable venting of flatus gasses combined with a highly effective de-odorization of the gasses before being released to the surroundings. Filters of various kinds are known for de-odorizing the vented flatus gasses. A recurring problem in connection with many of the known filter/venting arrangements is that the filter becomes clogged by liquid/slurry/solids present in the material discharged to the bag thereby giving rise to an unacceptable build-up of pressure in the bag during use. This problem is particularly serious for ileostomy patients because of the relatively liquid character of the discharged material.

Various different solutions to this problem have been proposed comprising the use of a barrier membrane interposed between the filter and the discharged material in the bag. The barrier membranes proposed are in many instances stated to be impermeable to liquids, permeable to gasses and having a liquid repelling surface facing the discharged material without dwelling on the more detailed characteristics necessary to obtain this in practice in a reliable and cost-effective manner.

As the bags typically are replaced daily or more often, the cost-effectiveness of the bags is very important while no compromises as regards the reliability of i.a. the venting and de-odorizing of the flatus gasses are acceptable. Therefore, any improvements increasing the reliability of the bag without substantially increasing the price, not to mention while decreasing the price, are extremely desirable and render any bag thus improved far superior to the prior art bags.

EP 0 443 728 B1 discloses a bag of the type in reference wherein the barrier membrane interposed between the filter and the interior of the bag comprises a thermoplastic, gas permeable, heat sealable or weldable film laminated together with a liquid impermable, gas permeable sheet of polytetrafluorethylene (PTFE). As the PTFE sheet is not heat sealable, the heat sealable or weldable film is necessary to heat seal or weld the membrane to an inner surface of the bag in a region surrounding the filter and venting aperture. The liquid repelling charateristics of PTFE are hereby exploited, but at the price of having to construct a laminate partly to reinforce the relatively fragile PTFE sheet and partly to allow a practical and reliable heat sealing of the membrane to the bag wall.

Apart from the complication and expense of having to laminate the two materials together and of the relatively expensive PTFE sheet, this solution is prone to delamination of the membrane with the consequent risk of rupture of the relatively fragile PTFE sheet and subsequent failure of the venting effect due to clogging of the filter by non-gaseous material passing through the ruptured region of the sheet.

The filter element disclosed in EP 0 443 728 B1 is in the form of a plane pad having two opposed surfaces and an edge surface and of the type where the flatus gasses flow through the pad in a direction substantially transverse to the opposed surfaces thereby affording a relatively low utilization of the filtering capability of the filter material because of short contact time between gasses and filter material and uneven flow rates through the different regions of the pad owing to unavoidable differences in flow resistance because of uneven thickness, uneven density and so on.

GB-A-2 059 797 discloses an odor absorbing gas venting filter assembly for being adhered to the inner wall of a collection bag of the type in reference. A barrier membrane is interposed between the filter pad and the interior of the bag, said barrier membrane being either a laminate or a cellulosic material coated with a water resistant layer and optionally supplemented with another film of various types. This filter assembly is relatively complicated to manufacture and is not reliable because of the inherent problems of lamination and coating as well as the fragile character of the cellulosic material. The flow path of the gasses through the filter pad is such that the filtering capability of the filter material is badly utilized.

A main object of the invention is to provide a bag of the type in reference that is reliable in use and relatively inexpensive and uncomplicated to manufacture and whereby the disadvantages of the known bags described above have been eliminated or substantially reduced.

According to the invention, this object is achieved by the barrier membrane comprising an unlaminated microporous film of ultra high molecular weight polyethelene (UPE), and the barrier membrane being adhered, preferably by heat sealing or welding, to said one wall.

Hereby, a relatively simple and inexpensive barrier membrane that is relatively tough and therefore relatively reliable as regards ruptures may be adhered to the inside of the wall of the pouch in a relatively uncomplicated manner as only one film of one material is to be handled and adhered, preferably by heat sealing, to the bag wall.

In addition to the problem of venting and de-odorizing the flatus gasses, it is highly desirable to remove at least some and preferably substantially all of the bacteria present in the flatus gasses before venting same. The applicant is not aware of any effort to deal specifically with this objective.

According to the invention, this object is attained by said film having a porosity substantially only allowing passage through the barrier membrane of particles in said gas flow having a maximum dimension smaller than 2 micrometers, preferably 1.9 micrometers, more preferably 1.8 micrometers, even more preferably 1.7 micrometers, further preferably 1.6 micrometers, further preferably 1.5 micrometers, further preferably 1.4 micrometers, further preferably 1.3 micrometers, further preferably 1.2 micrometers, further preferably 1.1 micrometers, further preferably 1.0 micrometers, further preferably 0.9 micrometers, further preferably 0.8 micrometers, further preferably 0.7 micrometers, further preferably 0.6 micrometers, further preferably 0.5 micrometers.

As most of the bacteria present in the human intestine or feces are larger than approx. 1 micrometer, many or all of said bacteria will be retained by the barrier membrane with a porosity as indicated above.

In the currently preferred embodiment, said film has a porosity substantially only allowing passage through the barrier membrane of particles in said gas flow having a maximum dimension smaller than 0.45 micrometers. Hereby, practically all human intestinal or feces bacteria are prevented from exiting the bag in the flow of flatus gasses. Such a membrane may be supplied by Millipore Corporation, Bedford, Mass. and according to U.S. Pat. No. 4,778,601 incorporated herein by reference.

Although constrained by the necessary total flow rate through the filter/venting arrangement that requires a certain maximum flow resistance per unit of surface area of the barrier membrane, the flow-through area of the barrier membrane may be so large that the porosity of the barrier membrane substantially only allows passage through the barrier membrane of particles in said gas flow having a maximum dimension smaller than 0.3 micrometers, preferably 0.2 micrometers. Hereby at least a substantial part of the human intestinal viruses are prevented from exiting the bag in the flow of flatus gasses. Such a membrane may also be supplied by Millipore Corporation.

It is also important for the cost-effectiveness and wearing comfort as well as the attractiveness of the filter/venting arrangement that the dimensions of the filtering element itself be kept to a minimum while providing for efficient and substantially constant filtering effect over a time period of typically at least 24 hours.

A filter/venting arrangement providing for an effective, reliable, relatively sterile and relatively inexpensive solution to these combined problems is therefore highly desirable.

In the preferred embodiment of the invention, the filter comprises a pad, a first surface of the pad facing the barrier membrane being covered by a gas impermeable film, preferably bonded thereto, such that the gas flow path through the filter pad extends from or to the circumferential edge thereof, the filter pad comprising at least two mutually superimposed layers of textile being highly, preferably nearly 100%, carbonized, each layer being bonded to an adjacent layer by means of a gas permeable adhesive film such as porous ethylene vinyl acetate (EVA).

It has turned out that a filter having this configuration is very superior to the filters currently in use in connection with pouches of the type in reference because the amount of activated carbon per unit of volume is at a maximum and the superimposition of at least two layers bonded by EVA affords a relatively long contact time between flatus gasses and filter material while substantially the entire mass of the filter is contacted by the flatus gasses with substantially the same flow intensity.

According to the invention, spacing means may be arranged between the filter and the barrier membrane so as to ensure a space therebetween for allowing a flow of gas in said space.

Hereby, it is ensured that as much as possible of the entire area of the barrier membrane available for passage of flatus gasses is utilized therefor by ensuring that abutment of the barrier membrane against the filter or the third film bonded to the filter does not limit flow of gasses through the barrier membrane.

In another aspect of the invention there is provided a filter/venting assembly for use in a bag or pouch for receiving discharge from the human body, said bag comprising:

a distal and a proximal wall, each of a gas and liquid impermeable, heat sealable or weldable thermoplastic material and having the edges thereof sealed together and defining the interior of the bag between the walls, the proximal wall having a stomal aperture, and one of the walls having a gas venting aperture spaced from the stomal aperture, the filter/venting assembly for de-odorizing gas vented through the gas venting aperture being adapted for being arranged such that all the gas exiting the bag through the venting aperture flows through the a filter element of the filter/venting assembly, the filter/venting assembly comprising:

an intermediate barrier membrane arranged intermediate the filter element and the interior of the bag such that all gas exiting the bag through the filter element flows through the barrier membrane and for preventing liquids and solids in the interior of the bag from contacting the filter element while allowing gas to flow through the barrier membrane from the interior of the bag to the filter element, the barrier membrane comprising an unlaminated microporous film of ultra high molecular weight polyethylene (UPE) having a porosity allowing retention by the barrier membrane of particles in said gas flow having a maximum dimension of 0.45 micrometers or more, the filter element comprising a pad, a first surface of the pad facing the barrier membrane being covered by a gas impermable film, preferably bonded thereto, such that the gas flow path through the filter element pad extends to or from the circumferential edge thereof, and the filter element pad comprising at least two mutually superimposed layers of textile being highly, preferably nearly 100%, carbonized, each layer being bonded to an adjacent layer by means of a gas permeable adhesive film, preferably of EVA.

In a further aspect of the invention, there is provided a method of venting flatus gasses from the interior of a bag or pouch for receiving discharge from the human body, said method comprising the step of preventing part and preferably substantially all of the human intestinal or fecal bacteria in said flatus gasses and/or feces from exiting from said bag with the vented flatus gasses, as well as a method of venting flatus gasses from the interior of a bag or pouch for receiving discharge from the human body, said method comprising the step of preventing part and preferably substantially all of the human intestinal or fecal viruses in said flatus gasses and/or feces from exiting from said bag with the vented flatus gasses.

The invention will now be explained more in detail and by way of example with reference to the drawings, wherein:

DRAWINGS

Figure 4:
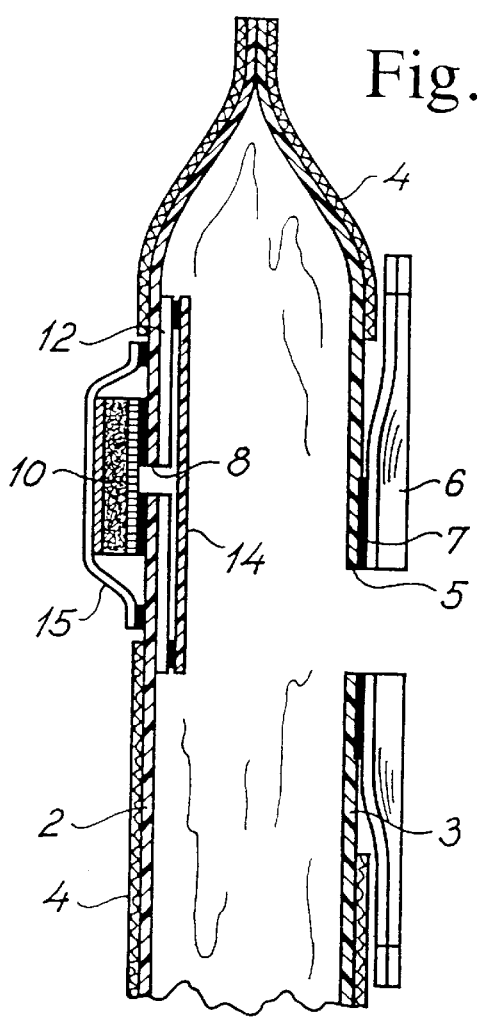
Figure 6:
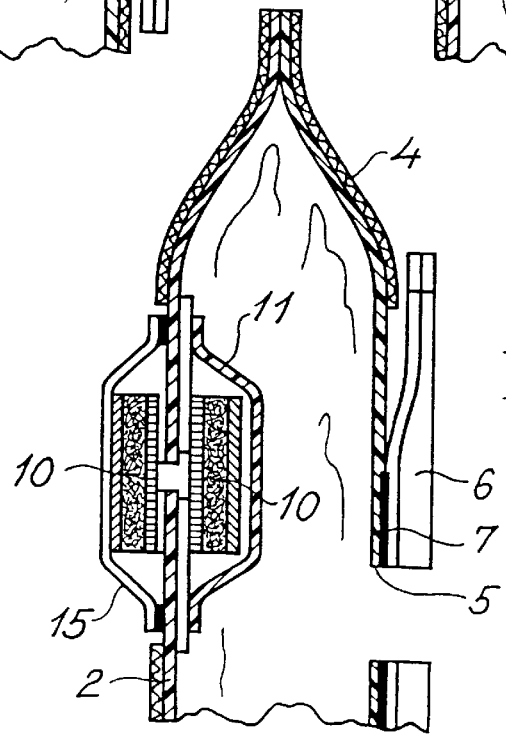
Figure 11:
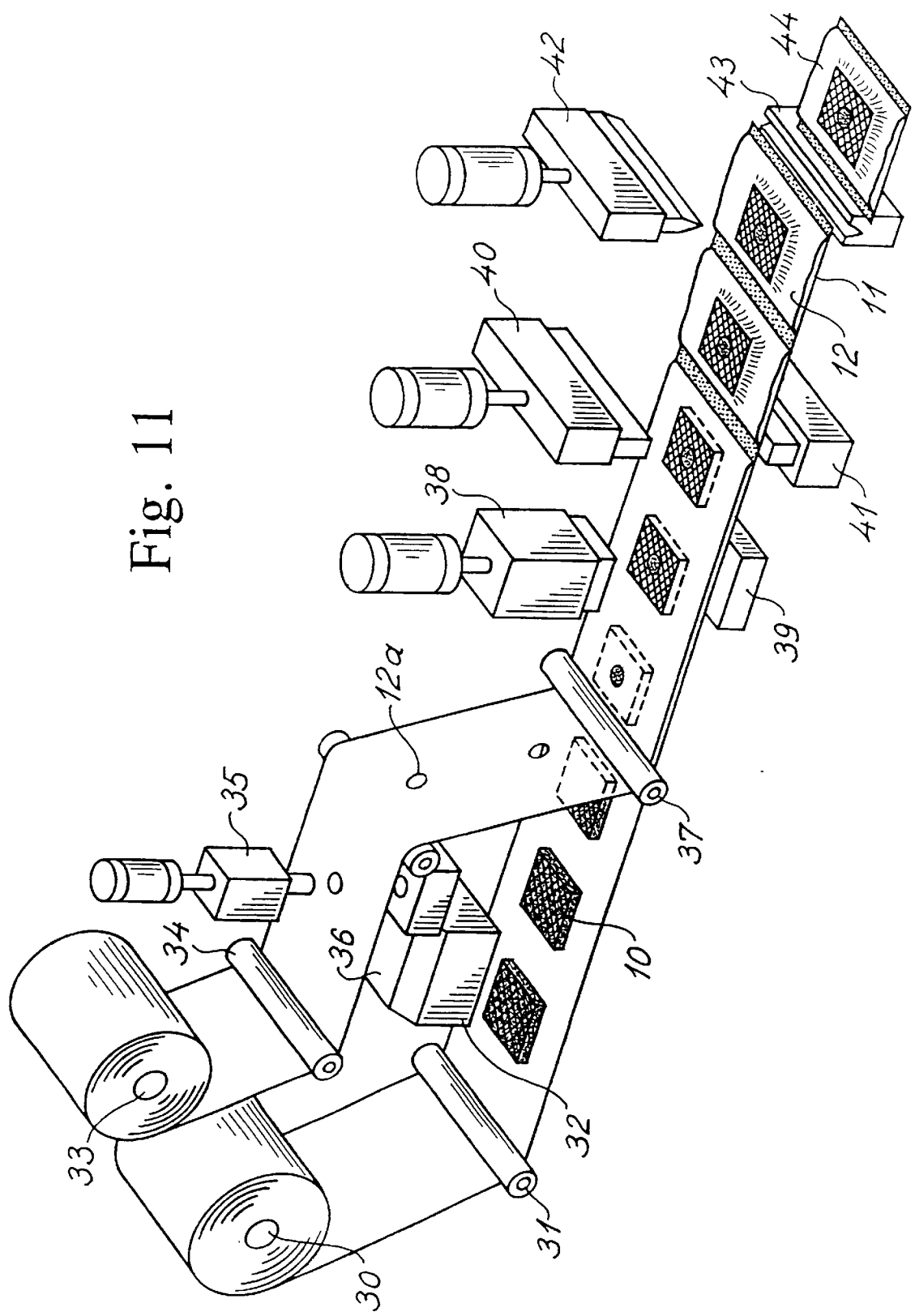

FIG. 1 shows a planar view of the currently preferred embodiment of a bag according to the invention seen from the distal wall, wherein the venting aperture is arranged, FIG. 2 shows a diagrammatical cross-sectional view of the upper region of the bag in FIG. 1 having a filter assembly package according to the invention adhered to the inner surface of the distal wall, FIG. 3 shows an enlarged diagrammatical cut away cross-sectional view of the filter assembly in FIG. 1 indicating the flow of flatus gas, FIG. 4 shows a diagrammatical cross-sectional view of the upper region of an alternative embodiment of a bag according to the invention having an alternative embodiment of a filter assembly package according to the invention adhered to the outer surface of the distal wall, FIG. 5 shows an enlarged diagrammatical cut away cross-sectional view of the filter assembly in FIG. 4 indicating the flow of flatus gas, FIG. 6 shows a view corresponding to FIGS. 2 and 4 of a double filter assembly having filter packages adhered to both the outer and inner surface of the distal wall of a bag according to the invention, FIGS. 7–10 show four alternative embodiments of a filter assembly according to the invention comprising four different embodiments of spacer means between the filter pad and the barrier membrane, and FIG. 11 shows a diagrammatical schematic elevational view of an application apparatus for producing a filter assembly according to the invention.

It should be noted that for the sake of clarity and illustration of the constructive details, the relative dimensions of the elements in FIGS. 2–11 are not correct, and the shapes and locations of the various elements relative to one another are distorted relative to reality where the films and elements conform much more to one another than as depicted.

DETAILED DESCRIPTION OF PREFERRED EMBODIMENTS

Referring now to FIGS. 1–3, a bag or pouch 1 is defined by two bag sheets heat sealed or welded together at the edges thereof and constituting a distal wall 2 and a proximal wall 3 of the bag 1. The bag sheets are made of five layers of film with a PVDC film sandwiched between two pairs of preferably EVA and/or PE film such that suitable gas and liquid impermeable heat sealable thermoplastic walls 2 and 3 are obtained.

A backing layer 4 of soft linen, felt or the like is attached to the outer surface of the distal and proximal walls 2 and 3 for the comfort of the user of the bag.

The proximal wall 3 is provided with a stoma aperture 5 surrounded by a skin friendly adhesion plate 6 for adhering the bag 1 to a patient and heat sealed at 7 to the proximal wall 3. The distal wall 2 is provided with a venting aperture 8 for venting flatus gasses from the interior of the bag 1 to the surroundings.

A heat sealed area indicated at 9 is provided in the backing layer 4 surrounding the venting aperture 8 so as to provide a suitably smooth surface for temporarily adhering a tear-off tab for closing the venting aperture 8 for preventing flow of water into the bag 1 through the aperture 8 when a patient wearing the bag 1 takes a bath.

A filter assembly package or unit comprises an activated carbon filter pad 10 sandwiched between a barrier membrane 11 of ultra high molecular weight polyethylene (UPE) and an approx. 100 micrometers thick support film 12 of polyethelene with 10% EVA having a venting aperture 12a with a diameter of approx. 5 mm. The filter assembly package is heat sealed to the inner surface of pouch wall 2 at 13.

Referring now to FIGS. 7–10, the filter pad 10 is a 20×20 mm$^2$ 100% active charcoal filter of the type FM7/250 supplied by Charcoal Cloth, UK having a thickness of approx. 1.3 mm. The charcoal textile consists of carbonized, woven viscose rayon textile. The carbonization takes place by means of a non-stochiometric process (low oxygen atmosphere to avoid burning of the material) at a temperature of 800–1000 degrees Celsius. The textile material of the pad consists of four layers interwoven in pairs, the pairs of layers 14 and 15 being adhered to one another by means of a gas permeable layer 16 of adhesive of polyurethane or EVA configured as a porous net.

The charcoal filter is impregnated with a 5% w/w solution of copper so as to obtain a more rapid and better adsorption of flatus gasses as well as with a 5% w/w solution of fluor to bind/retain the carbon particles in the material i.a. to avoid carbon dust.

The charcoal layers 14 and 15 are laminated to films 17 and 18, respectively, forming opposed outer surfaces of the filter pad. The film 17 is gas permeable and consists of a PE nonwoven material adhered to the charcoal layer 14 by means of an EVA adhesive configured as a porous net, while the film 18 is gas impermeable and consists of a material containing PVDC adhered to the charcoal layer 15 by means of an EVA adhesive.

The charcoal filter is not or only partly liquid repelling in itself, but it is extremely efficient as a de-odorizing filter. The carbonized textile layers contain 0.16–0.18 g carbon (dry) and according to the modified British Standard testing method BS 7120, the filter adsorbs more than 30–40 l gas mixture, 30 ppm H2S in N2. A corresponding test with (CH3)2S shows that the filter can adsorb more than 40–60 l gas mixture, 30 ppm (CH3)2S in N2. The filter has a back pressure of max. 4.5 mBar with a gas flow therethrough of 100 ml/min at a pressure of 0.1 Bar. This low back pressure allows the flatus gasses to flow relatively quickly through the filter, thus avoiding ballooning of the bag 1.

The ultra high molecular weight polyethelene barrier membrane 11 is supplied by Millipore Corporation, Bedford, Mass., USA and is according to U.S. Pat. No. 4,778,601 incorporated herein by reference. It has a pore volume of 70–80% and such that substantially all particles in the flatus gasses with a maximum dimension of 0.45 micrometers cannot pass through the barrier membrane, i.e. are retained thereby such that such particles cannot pass to the filter pad 10 from the interior of the pouch 1. The thickness of the barrier membrane 11 is 148 micrometers plus/minus 20 micrometers. The size is approx. 32×32 mm. The Flow Time is in the range of approx. 150 sec/500 ml to approx. 300 sec/500 ml in 100% IPA (applied to a circular membrane with a diameter of 47 mm at a pressure of 14.2 psi). Porosity determined by the Bubble Point Method is in the range of approx. 15 psi to approx. 21 psi in 100% IPA.

The support film 12 is wider than the filter pad and is heat sealed or adhered to the film 17 of the filter pad 10 such that the aperture 12a is centrally located relative to the filter pad.

The film 17 of the filter pad 10 is heat sealed/adhered to the support film 12 such that a circular non-sealed or non-adhered area of the filter pad larger than the 5 mm aperture 12a is centrally located around the aperture 12a. The barrier membrane 11 is arranged over the filter pad 10 on the opposite side and is heat sealed/adhered to the support film 12 so that the filter pad 10 is enclosed in a package comprising on one side a gas permeable, liquid impermeable membrane 11 and on the other side a heat sealable PE support film 12 with a central venting aperture 12a.

The filter package may thereafter be attached to the bag wall 2 in which a venting aperture 8 smaller than aperture 12a has been punched. The attachment to the inner surface of the wall 2 may either be accomplished by rim welding/heat sealing of the support film 12/membrane 11 to the wall 2 at 13 or by adhering the package to said wall 2 with a suitable adhesive.

The UPE membrane 11 has a smooth, soft surface and the surface tension has been measured to be 36 mN/m according to ISO 8296 (1987), while contact angle measurements according to the Wihelmy Plate Technique show that the surface of the membrane is similar to Teflon as regards friction. Therefore the ability of the membrane surface to repel liquid is such that a film of liquid preventing gas from passing through the membrane is not formed on the surface thereof. The pore volume of the membrane material of 70–80% and the structure (see FIGS. 12–16) with very narrow passages only allowing particles smaller than 0.45 micrometers to pass therethrough entails that the flatus gas easily may pass through while human intestinal or fecal bacteria in the flatus gas or feces are retained by the membrane 11.

Furthermore, liquids are prevented from flowing through the membrane. Laboratory measurements where the membrane was loaded with 700 mm water column showed that no water flowed through, and no droplets were formed on the surface even after a test duration of 8 days.

An Artificial Stool Test (Applicants' test method) consisting in filling bags 1 with artificial stool and inverting the bags so that the filter assembly was covered by artificial stool during 24 hours while observing whether artificial stool passed through the membrane gave excellent results. The artificial stool is composed of beans, salts, intestinal enzymes and other substances equivalent to the contents of the human intestine such that the test simulates the influences on the membrane in practice.

The barrier membrane 11 has a back pressure of approx. 2–3 mBar with an air flow therethrough of 100 ml/min at a pressure of 0.1 Bar.

Referring now to FIG. 3, the gas flow through the filter assembly is indicated by means of arrows, the gas flowing through the membrane 11 and into the filter pad 10 from the periphery thereof towards the centre thereof and out through the aperture 8 in the wall 2.

Referring now to FIGS. 4–5, an alternative arrangement of the filter assembly on the outer surface of the wall 2 is shown, the same references indicating the same elements as in FIG. 2. The filter pad 10 is adhered to the outer surface of the wall centrally located around the venting aperture 8. A barrier membrane 14 of UPE material identical to the material of barrier membrane 11 in FIG. 2 is heat sealed or welded with the support film 12 to the inner surface of the wall 2. The filter pad 10 is covered by a protection membrane 15 of a gas permeable, liquid impermeable material that may be the same UPE material as the material of the membrane 14 or any other suitable material. The flow of flatus gasses through the filter assembly is indicated by the arrows in FIG. 5.

Referring now to FIG. 6, another alternative embodiment of a filter assembly according to the invention combining the embodiments of FIGS. 2 and 4 is shown.

It will be obvious to those skilled in the art that other filter designs may be employed and that the location and number of filter pads may be varied relative to the venting aperture. Furthermore, several venting apertures may be arranged in the wall 2 combined with one or more filter pads.

Referring now again to FIGS. 7–10, various embodiments of spacing means arranged between the filter pad 10 and the barrier membrane 11 are illustrated, the spacing means ensuring a gas flow space between the filter pad 10 and the barrier membrane 11. In FIG. 7 ridges or peaks 20 are formed in the surface of the film 18 or applied thereto. In FIG. 8 ridges or peaks 21 are formed in the surface of the barrier membrane 11 or applied thereto. In FIG. 9 filaments or spheres 22 are adhered to either the film 18 or the membrane 11. In FIG. 10 a layer of open cell foam material is adhered to either the film 18 or the membrane 11. In all embodiments it is obtained that substantially the entire area of the barrier membrane 11 is available for flow of flatus gasses to the filter pad 10.

Referring now to FIG. 11, an apparatus for producing a filter assembly according to the invention and as shown in FIG. 2 is shown schematically and diagrammatically.

A supply roll 30 of the barrier membrane 11 feeds the membrane in a continuous web over an idler roller 31 below a locating device 32 for locating filter pads 10 on the membrane web with a predetermined spacing. A second supply roll 33 of the support film 12 feeds the support film in a continuous web over an idler roller 34 below a punching device 35, 36 for punching holes 12a in the support film spaced corresponding to the spacing of the filter pads 10. The punched support film continues over an idler roller 37 such that the support film is superimposed on the membrane 11 and the filter pads 10 with the holes 12a centrally located relative to the pads 10.

A heat sealing device 38, 39 heat seals the support film 12 to the gas impermeable film 17 of the filter pad 10 and thereafter a heat sealing device 40, 41 heat seals the support film 12 to the membrane 11 whereafter a cutting device 42, 43 cuts the combined support film 12 and membrane 11 in the middle of the heat seal performed by the device 42, 43 such that individual filter assembly packages 44 are formed ready for being attached to the wall 2 of the bag 1.

The heat sealing is carried out carefully to avoid compression of the relatively brittle filter cloth, so as to avoid crushing same. The pressure exerted by the device 38, 39 is only 4 kg at 3–4 Bar corresponding to a total filter welding pressure of only 0.15–0.20 N/mm$^2$ (filter surface).

It should be understood that while the shown and described pouch 1 is entirely closed by a total welding or heat sealing around the entire periphery, the pouch may also be of the type having a drainage aperture provided by not welding the lower edge regions at the two bag sheets to each other.

I claim:

1. A filter assembly for an ostomy bag having a gas venting aperture for venting gases from the interior of such bag, said filter assembly comprising a filter pad and a gas permeable barrier membrane extending over a first interior-facing surface of said filter pad for preventing liquid and solid waste from contacting said filter pad; said barrier membrane comprising an unlaminated microporous film of ultra high molecular weight polyethylene having a porosity allowing passage through said membrane of gas-carried particles having a maximum dimension smaller than 0.45 micrometers.

2. The filter assembly of claim 1 in which said microporous film has a porosity allowing passage through said barrier membrane only of particles in said gas flow having a maximum dimension smaller than 0.2 micrometers.

3. The filter assembly of claims 1 or 2 wherein said assembly is combined with an ostomy bag having a distal wall and a proximal wall with edges thereof sealed together and defining the interior of the bag between said walls; said proximal wall having a stomal aperture and one of said walls having a gas venting aperture spaced from the stomal aperture; said filter pad having a second surface opposite from said first surface and secured to said one wall about said venting aperture so that all of the gas exiting the bag through said gas venting aperture flows through said filter; said barrier membrane being disposed intermediate said filter pad and the interior of said bag such that all of the gas exiting the bag through said filter pad and through said venting aperture flows through said barrier membrane.

4. The combination of claim 3 in which said barrier membrane is heat sealed or welded to said one wall.

* * * * *